United States Patent
Phillips

(10) Patent No.: US 7,630,766 B2
(45) Date of Patent: Dec. 8, 2009

(54) EXERCISE RESPONSIVE PACEMAKER TUNING METHOD USING DOPPLER BLOOD FLOW MEASUREMENTS TO ADJUST PACING FOR OPTIMIZED FLOW

(75) Inventor: Robert Allan Phillips, Coffs Harbour (AU)

(73) Assignee: USCOM Limited, Sydney, New South Wales (AU)

( * ) Notice: Subject to any disclaimer, the term of this patent is extended or adjusted under 35 U.S.C. 154(b) by 525 days.

(21) Appl. No.: 10/519,863

(22) PCT Filed: Jun. 26, 2003

(86) PCT No.: PCT/AU03/00807

§ 371 (c)(1),
(2), (4) Date: Dec. 29, 2004

(87) PCT Pub. No.: WO2004/004827

PCT Pub. Date: Jan. 15, 2004

(65) Prior Publication Data

US 2005/0245981 A1    Nov. 3, 2005

(30) Foreign Application Priority Data

Jul. 3, 2002    (AU) .................................. PS3355

(51) Int. Cl.
*A61N 1/365* (2006.01)
(52) U.S. Cl. .............. 607/19; 607/24; 607/27; 607/3
(58) Field of Classification Search ............. 607/27, 607/19
See application file for complete search history.

(56) References Cited

U.S. PATENT DOCUMENTS

| | | | |
|---|---|---|---|
| 3,675,640 | A | 7/1972 | Gatts |
| 3,980,075 | A | 9/1976 | Heule |
| 4,413,629 | A | 11/1983 | Durley |
| 4,671,295 | A | 6/1987 | Abrams et al. |
| 4,796,634 | A | 1/1989 | Huntsman et al. |
| 4,807,636 | A | 2/1989 | Skidmore et al. |
| 4,858,614 | A | 8/1989 | Stevens et al. |
| 4,866,613 | A | 9/1989 | Amemiya et al. |
| 4,867,165 | A | 9/1989 | Noller et al. |
| 4,945,909 | A * | 8/1990 | Fearnot et al. ............. 607/14 |

(Continued)

FOREIGN PATENT DOCUMENTS

DE    43 20 519    1/1995

(Continued)

OTHER PUBLICATIONS

"Relations of Doppler Stroke Volume and Its Components to Left Ventricular STroke Volume in Normotensive and Hypertensive American Indians," American Journal of Hypertension, 1997, 10, 619-628.*

(Continued)

*Primary Examiner*—Kennedy J Schaetzle
(74) *Attorney, Agent, or Firm*—Merchant & Gould P.C.

(57) ABSTRACT

A method of tuning a cardiac prosthetic pacing device includes (a) monitoring the flow output from the heart, and (b) adjusting the timing of pacing events by the cardiac prosthetic pacing device so as to optimise the flow from the heart under operational conditions.

7 Claims, 6 Drawing Sheets

U.S. PATENT DOCUMENTS

| | | | |
|---|---|---|---|
| 5,020,516 A | 6/1991 | Biondi et al. |
| 5,052,395 A | 10/1991 | Burton et al. |
| 5,086,776 A | 2/1992 | Fowler, Jr. et al. |
| 5,139,020 A | 8/1992 | Koestner et al. |
| 5,152,291 A | 10/1992 | Dias |
| 5,183,040 A | 2/1993 | Nappholz et al. |
| 5,188,106 A | 2/1993 | Nappholz et al. |
| 5,241,966 A | 9/1993 | Finkelstein et al. |
| 5,265,615 A | 11/1993 | Frank et al. |
| 5,313,947 A | 5/1994 | Micco |
| 5,361,771 A | 11/1994 | Craine et al. |
| 5,389,217 A | 2/1995 | Singer |
| 5,447,164 A | 9/1995 | Shaya et al. |
| 5,546,943 A | 8/1996 | Gould |
| 5,584,298 A | 12/1996 | Kabal |
| 5,634,467 A | 6/1997 | Nevo |
| 5,640,960 A | 6/1997 | Jones et al. |
| 5,891,036 A | 4/1999 | Izumi |
| 5,891,176 A * | 4/1999 | Bornzin ............... 607/18 |
| 6,106,472 A | 8/2000 | Chiang et al. |
| 6,149,587 A | 11/2000 | Raines |
| 6,217,522 B1 | 4/2001 | Shoshan |
| 6,234,963 B1 | 5/2001 | Blike et al. |
| 6,285,898 B1 | 9/2001 | Ben-Haim |
| 6,292,689 B1 | 9/2001 | Wallace et al. |
| 6,315,730 B1 | 11/2001 | Hoff et al. |
| 6,468,219 B1 | 10/2002 | Njemanze |
| 6,506,157 B1 | 1/2003 | Teigman et al. |
| 6,511,413 B2 | 1/2003 | Landesberg |
| 6,522,923 B1 * | 2/2003 | Turcott ............... 607/27 |
| 6,527,722 B1 | 3/2003 | Fazioli et al. |
| 6,530,887 B1 | 3/2003 | Gilbert et al. |
| 6,565,513 B1 | 5/2003 | Phillips |
| 6,569,101 B2 | 5/2003 | Quistgaard et al. |
| 6,577,901 B2 | 6/2003 | Thompson |
| 6,580,946 B2 | 6/2003 | Struble |
| 6,685,621 B2 | 2/2004 | Bolling et al. |
| 6,776,764 B2 | 8/2004 | Pinsky |
| 7,024,244 B2 | 4/2006 | Muhlenberg et al. |
| 7,092,758 B2 * | 8/2006 | Sun et al. ............... 607/18 |
| 7,144,365 B2 | 12/2006 | Bolling et al. |
| 7,164,948 B2 * | 1/2007 | Struble et al. ............... 607/22 |
| 7,192,403 B2 | 3/2007 | Russell |
| 2002/0091319 A1 | 7/2002 | Moehring et al. |
| 2002/0138512 A1 | 9/2002 | Buresh et al. |
| 2003/0100925 A1 | 5/2003 | Pape et al. |
| 2003/0163056 A1 | 8/2003 | Osypka et al. |
| 2003/0195409 A1 | 10/2003 | Seitz et al. |
| 2003/0199779 A1 | 10/2003 | Muhlenberg et al. |
| 2004/0254483 A1 | 12/2004 | Zdeblick et al. |

FOREIGN PATENT DOCUMENTS

| | | |
|---|---|---|
| EP | 0 420 085 | 4/1991 |
| EP | 0 474 957 | 3/1992 |
| EP | 0 503 285 | 9/1992 |
| EP | 0706777 | 10/1995 |
| EP | 1 103 217 | 5/2001 |
| EP | 1 250 889 | 10/2002 |
| EP | 1 304 074 | 4/2003 |
| GB | 1 461 345 | 1/1977 |
| WO | WO 89/04634 | 1/1989 |
| WO | WO 92/06633 | 4/1992 |
| WO | 95/19806 | 7/1995 |
| WO | WO 96/01586 | 1/1996 |
| WO | WO 96/32888 | 10/1996 |
| WO | WO 97/12547 | 4/1997 |
| WO | 99/66835 | 12/1999 |
| WO | 00/62858 | 10/2000 |
| WO | WO 01/48451 | 7/2001 |
| WO | WO 03/015609 | 2/2003 |

OTHER PUBLICATIONS

Nidorf et al. "New Prespectives in the Assessment of Cardiac Chamber Dimensions During Development and Adulthood." *JACC* vol. 19. No. 5. 1992. pp. 983-988.

* cited by examiner

EXERCISE RESPONSIVE PACEMAKER TUNING METHOD USING DOPPLER BLOOD FLOW MEASUREMENTS TO ADJUST PACING FOR OPTIMIZED FLOW

FIELD OF THE INVENTION

The present invention relates to the field of cardiac pacemakers and, in particular, discloses a methodology and apparatus for selectively tuning a pacemaker-type device.

BACKGROUND OF THE INVENTION

Pacemaker devices normally consist of the pacemaker control unit containing a power cell such as a battery, a pacemaker lead and end electrodes which are attached to the heart so as to stimulate the heart into action at certain timed occurrences. Recent advances in pacemaker technology include providing for fully programmable capabilities. Modern pacemaker devices such as those available from Medtronic Inc often include on board processing and storage capabilities and the latest models allow for external communication with reader and control devices located outside the body for telecommunications. Examples of such systems are disclosed in U.S. Pat. No. 6,577,901 to Thompson, U.S. Pat. No. 6,580,946 to Struble and U.S. Patent Application 2003/0100925 to Pape et al. the contents of each of which is incorporated by cross reference disclose suitable forms of heart pacemaker technology suitable for us with the present invention.

As is disclosed in the aforementioned patents, modern pacemaker devices also allow for a variability in operation of the heart in accordance with external needs. For example, during exercise, the pacemaker device may increase the heart rate. Further, during periods of rest, the pacemaker device may decrease the heart rate. Further, programmable pacemakers allow for storage of information for downloading as to the onboard operation of the pacemaker unit.

There is therefore a general need to accurately and succinctly tune the pacemaker unit for the proper operation of the heart muscle.

SUMMARY OF THE INVENTION

It is an object of the present invention to provide for a method and apparatus for tuning the operation of pacemaker units to achieve more optimal results.

In accordance with a first aspect of the present invention, there is provided a method of tuning a cardiac prosthetic pacing device, the method comprising the steps of (a) monitoring the flow output from the heart; and (b) adjusting the timing of pacing events by the cardiac prosthetic pacing device so as to optimise the flow from the heart under operational conditions.

Preferably, the method includes monitoring the flow utilising a continuous wave Doppler signal directed at the heart. Ideally, the method is repeated under a number of different operational conditions for a patient including walking and/or running. Further, preferably the method is repeated under a number of different pharmalogical conditions for a patient.

In accordance with a further aspect of the present invention, there is provided an apparatus for tuning a cardiac prosthetic pacing device, the apparatus including: monitoring means for non invasively monitoring the flow of blood out of the heart; control means for controlling the operation of the cardiac prosthetic pacing device including variation of the pacing rate; and processing means interconnected to the monitoring means and the control means, the processing means instructing the control means to vary the pacing rate of the cardiac prosthetic pacing device and monitor the corresponding measurement of the monitoring means.

Preferably, the monitoring means includes a continuous wave Doppler sensor device for emitting and receiving a CW-Doppler signal directed and reflected from the patient's heart.

BRIEF DESCRIPTION OF THE DRAWINGS

Preferred embodiments of the invention will now be described, by way of example only, with reference to the accompanying drawings in which.

DESCRIPTION OF PREFERRED AND OTHER EMBODIMENTS

In the preferred embodiment, continuous wave ultrasound techniques are utilised to transcutaneously measure the cardiac output of a heart operating with a cardiac prosthetic pacing device. Through utilisation of ultrasound techniques, a measurement of cardiac output can be obtained as a function of rate and volume. The ultrasound techniques also provide a measure of stroke volume thereby providing information for optimisation of settings of the pacemakers.

Figure 1:
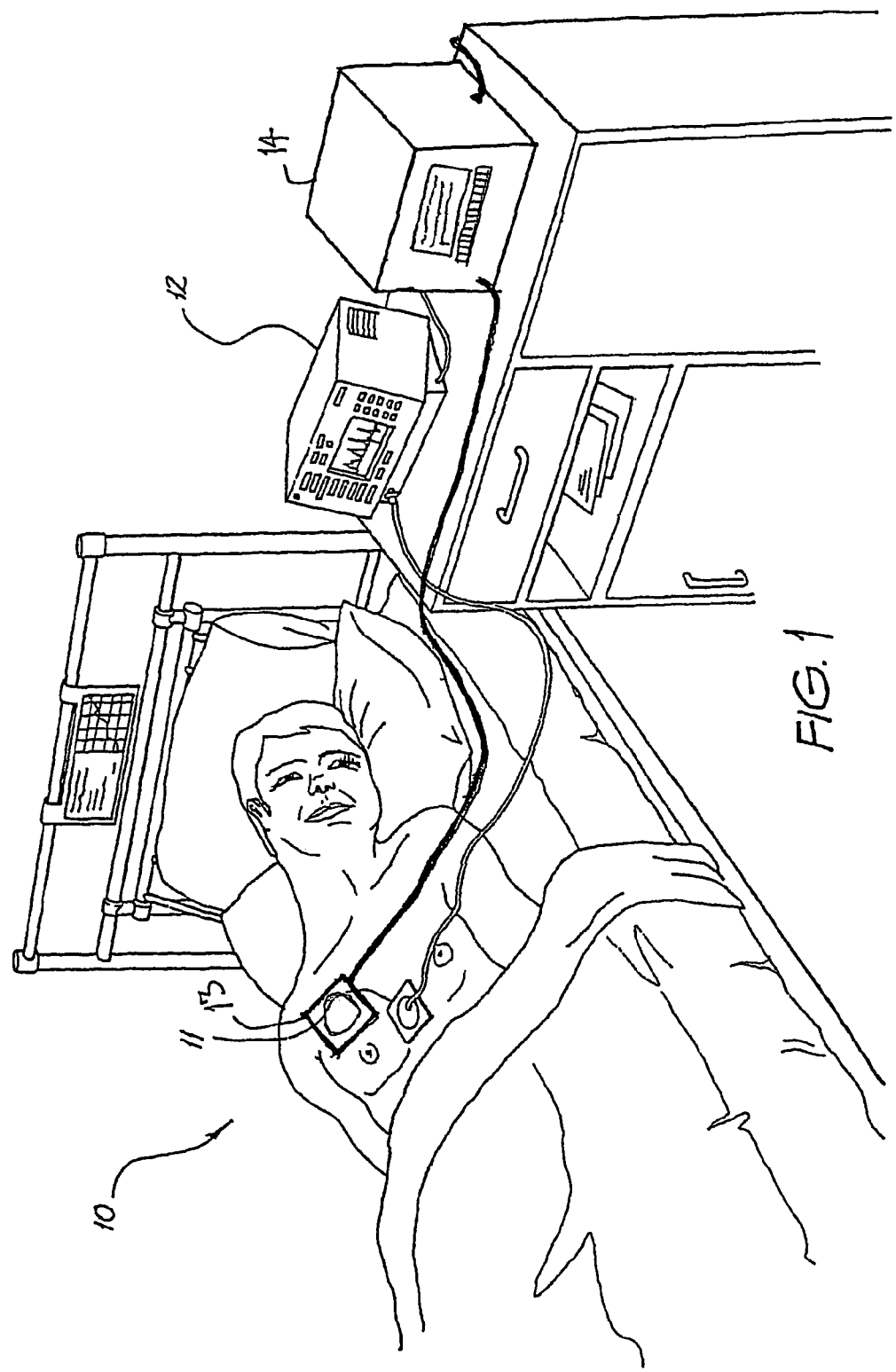
FIG. 1 illustrates a first operational environment of the preferred embodiment.

Turning initially to FIG. 1, there is illustrated one arrangement utilising the preferred embodiment. In this arrangement, a patient 10 has attached two non-invasive monitoring devices 11-13. Each of the two devices 11-13 are interconnected to a processing and display unit eg. 12, 14. Each of the units 12, 14 includes an internal computer processing means, a display and a series of control buttons for controlling the functionality of the device. Each of the devices 12, 14 are further networked to a base station or the like for overall monitoring and control.

The sensor 13 is in telemetry connection with the heart pacemaker unit. It is assumed that the device 14 in conjunction with sensor 13 is able to vary the rate at which the heart paces. Such systems are disclosed in the aforementioned patent applications.

Hence, variations in blood flow around the body can be measured by alteration of the heart pacemaker timing period whilst simultaneously monitoring the corresponding alteration in blood flows as detected by the CW transducer device. In this manner the pacing period can be optimised for the particular recipient by estimation of the flow requirements of the recipient given their size, weight etc.

Figure 2:
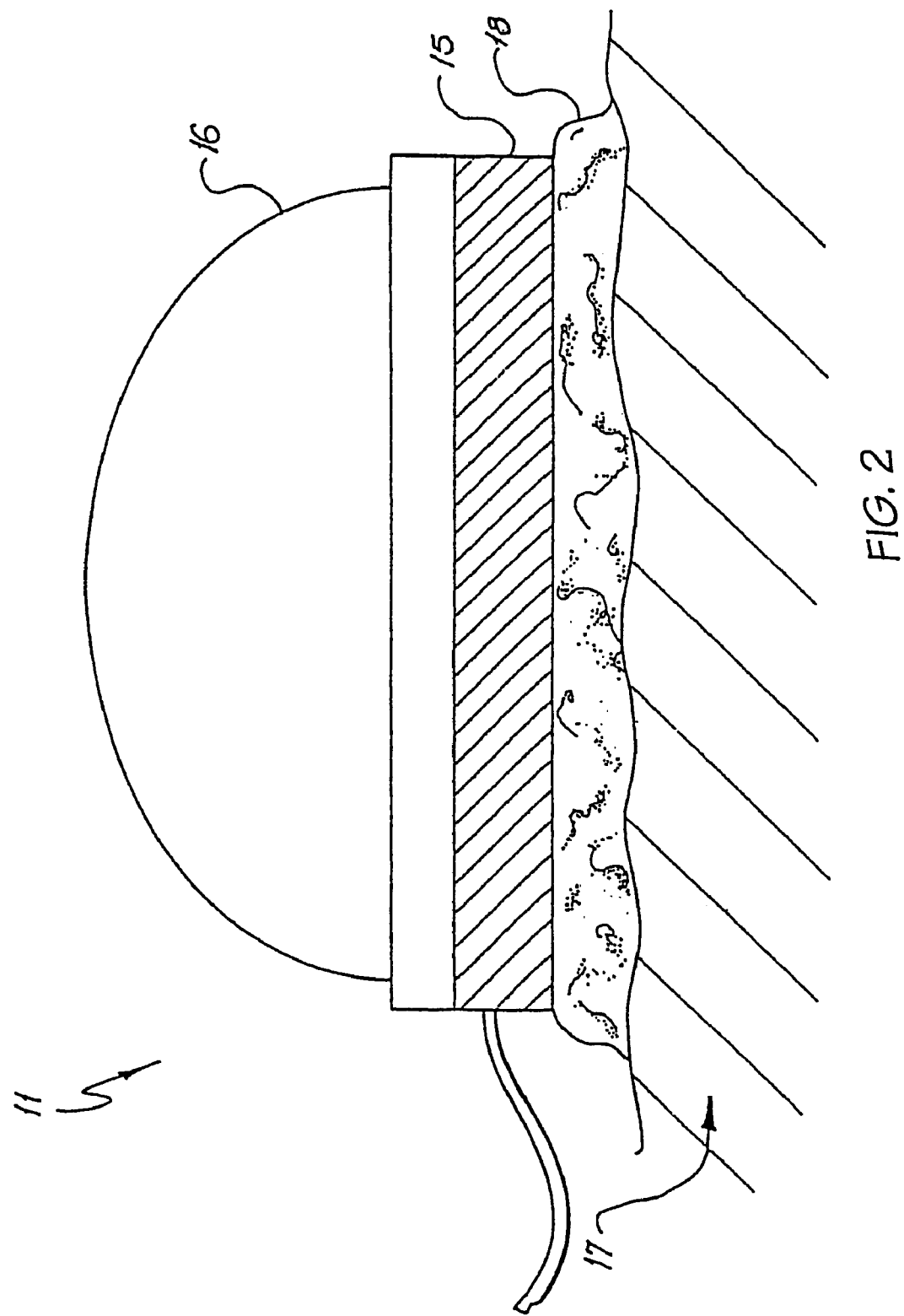
FIG. 2 illustrates a sectional view through a transducer device.

FIG. 2 shows an example of the first actuator 11 for attachment to the skin surface. Ideally CW Doppler is utilised to monitor the blood flow within the heart. CW Doppler is a non-invasive technique in which ultrasonic signals from transducer elements are directed into a blood carrying vessel of a patient. Doppler shifts in the reflected signal provide an indication of the rate of blood flow. In FIG. 2, a transducer element 11 includes an ultrasonic transducer 15 attached to a positioning device 16 which can be used to initially set the position of the transducer. Between the transducer 15 and a patient's skin 17 is placed a gel coupling layer 18 for coupling the ultrasonic transducer vibrations to the skin 17. The principles of CW Doppler flow measurement are known. Patent Cooperation Treaty (PCT) publication number WO 99/66835 to the present assignee, the contents of which are incorporated herein by cross-reference, describes in more detail an ultrasonic transducer device suitable for measuring blood flow using the CW Doppler method.

In the embodiment shown in FIG. 1, the transducer elements are placed on the patient to obtain intra-cardiac or aortic signals, for example through a suprasternal notch.

Figure 3:
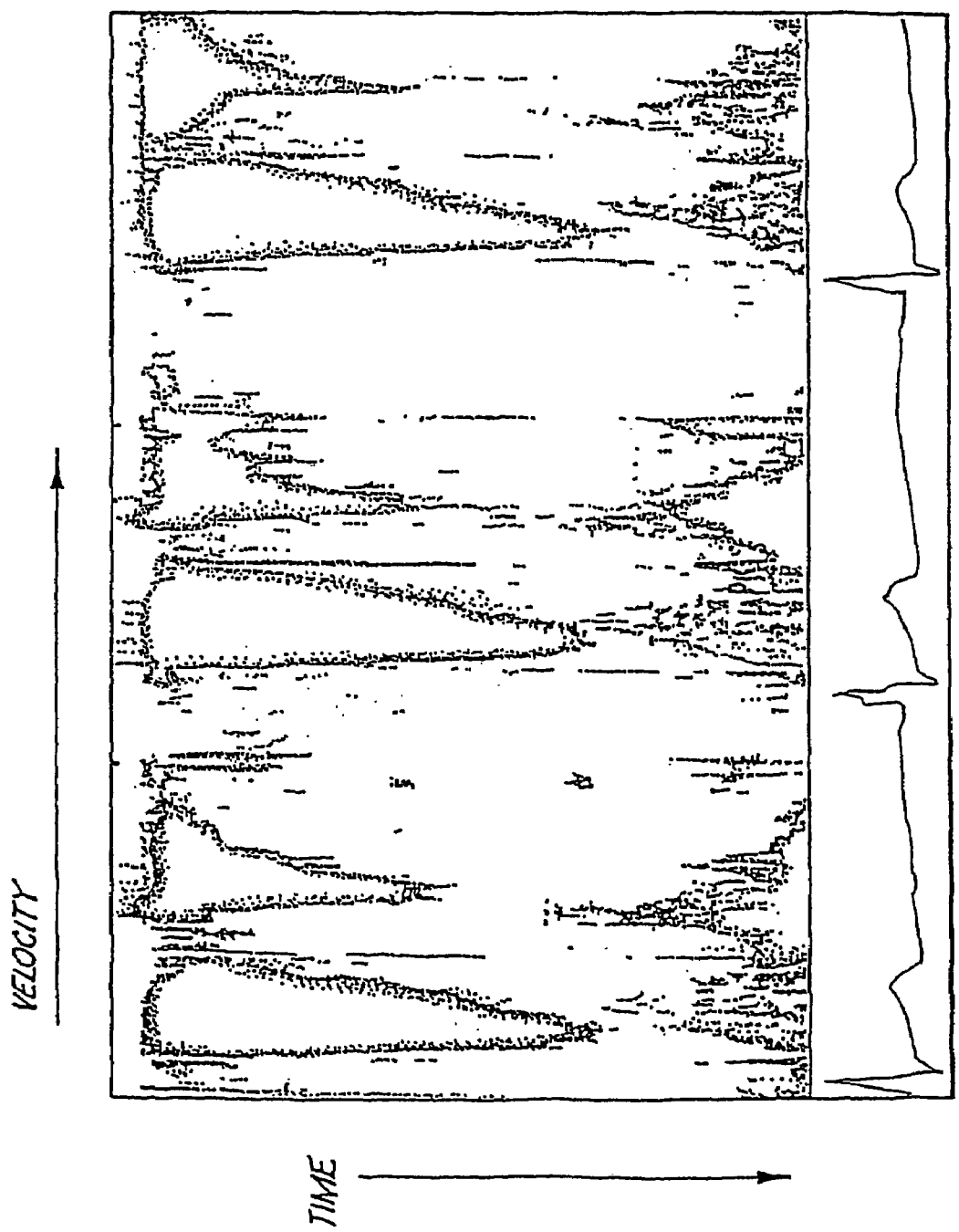
FIG. 3 illustrates a velocity time snapshot as measured by the CW transducer device.
Figure 4:
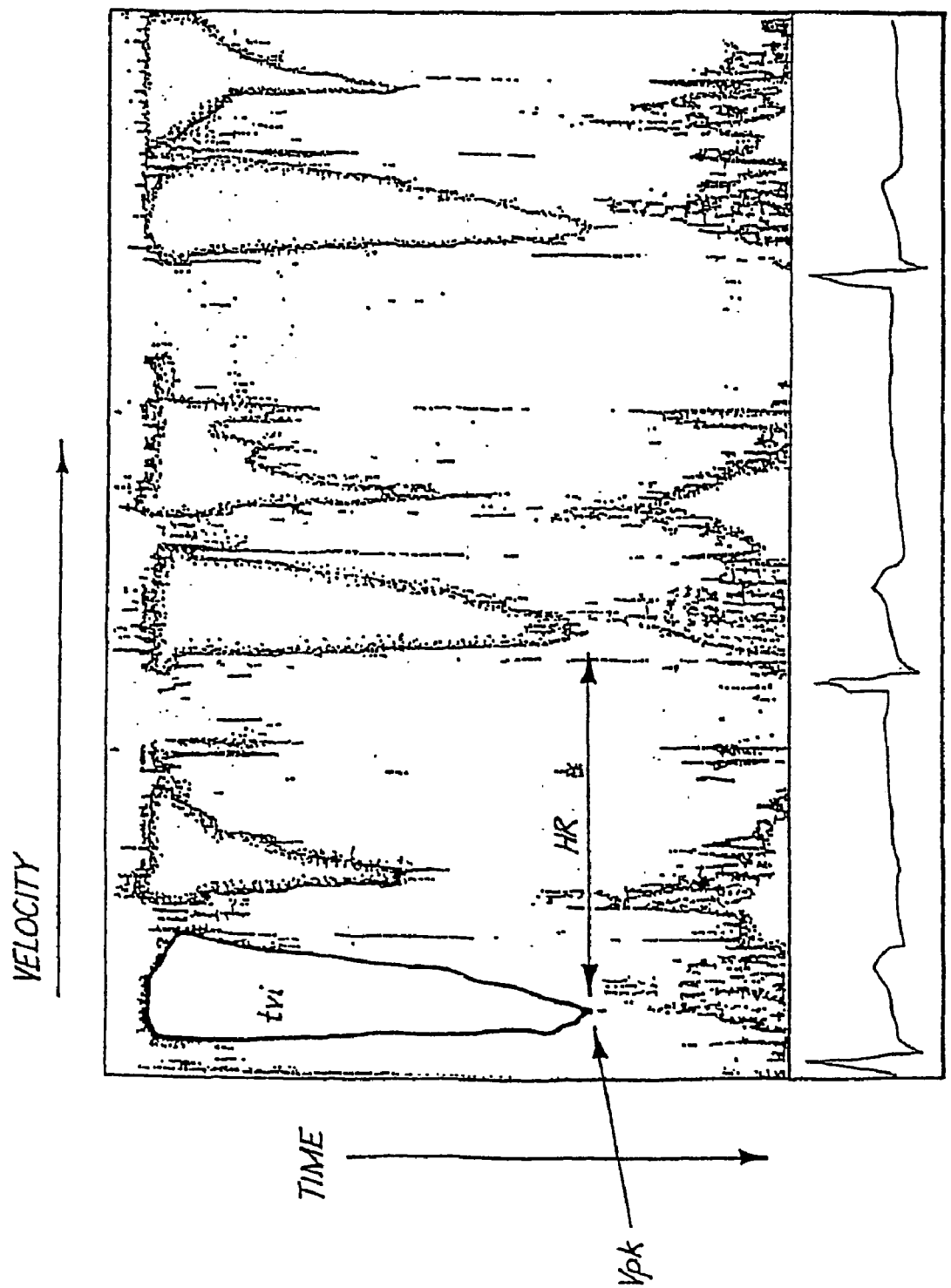
FIG. 4 illustrates various portions of the snapshot of FIG. 3.

The CW method detects the velocity of individual blood cells by measuring the frequency change of a reflected ultrasound beam and displaying this as a velocity time flow profile, an example of which is shown in FIG. 3. The transducer output forms an input to the processor unit which image processes the results of FIG. 3 so as to calculate from the velocity time flow profile, the velocity time integral (tvi) and other relevant information such as heart rate (HR) and peak volume Vpk. These calculations can then be compared with the pacemaker timing setting to determine an overall optimal performance.

The arrangement of FIG. 1 can then be translated into other real life situations. For example with the patient on a walking treadmill and a running treadmill. Again, measurements can be taken of variation in blood flow pumping rates with variation in heart rates so as to thereby tune the operation of the pacemaker unit for the particular individual to particular activities. These results can then be stored in the pacemaker unit for future use.

Figure 5:
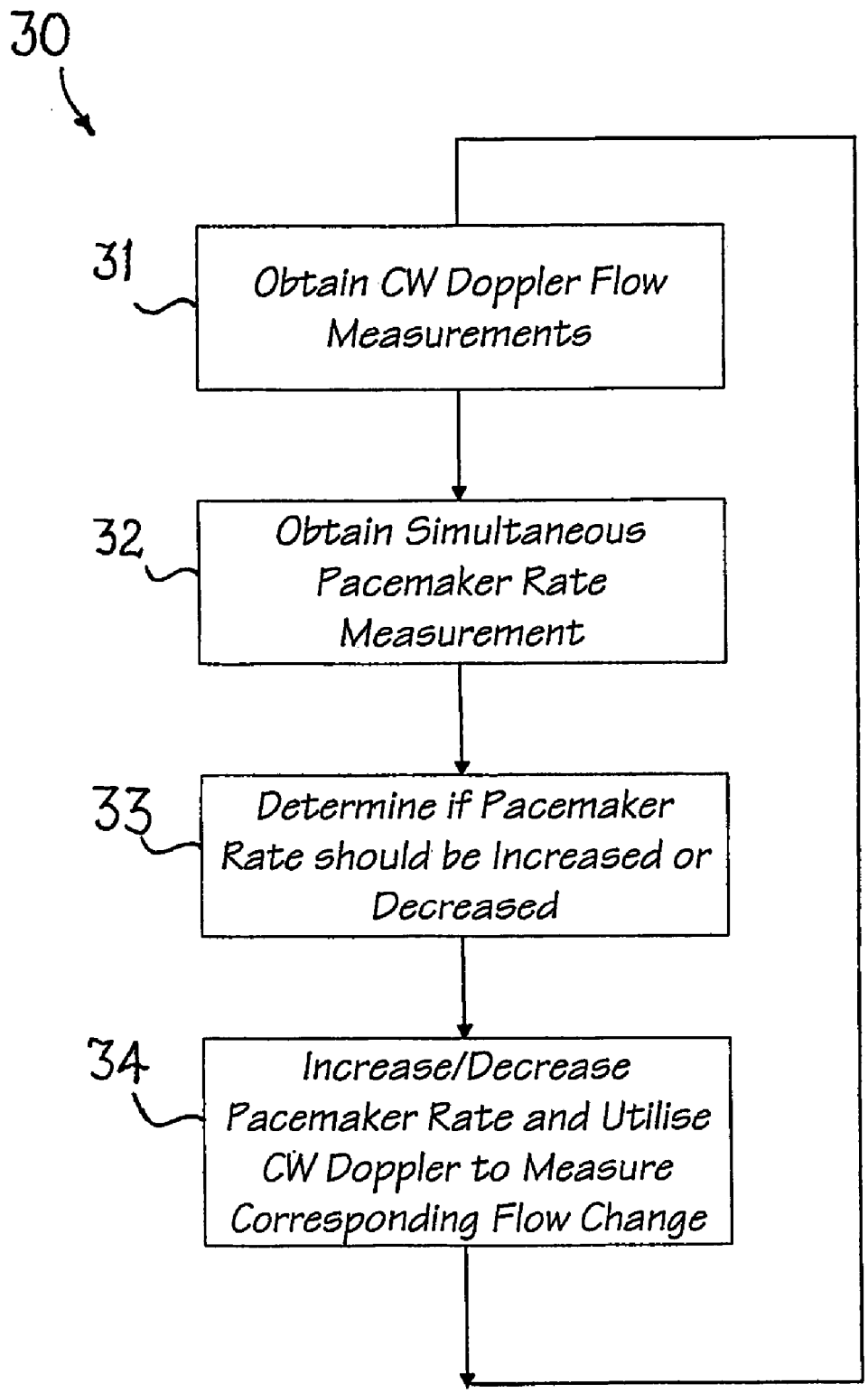
FIG. 5 and FIG. 6 illustrates flowcharts of the steps involved in optimising the pacemaker arrangement of the preferred embodiment.

A flow chart of the overall steps involved in the operation of the preferred embodiment is illustrated generally 30 in FIG. 5. These include the steps of obtaining a CW Doppler flow measurement 31 and simultaneously obtaining pacemaker rate measurements 32. Next, a determination is made as to whether to increase or decrease the pacemaker rate measurement 33. Upon increasing or decreasing measurements, continual analysis of the change in flow rate is made 34.

Through the utilisation of flow measurements via the CW technique, advanced analysis can also be conducted in a more non invasive manner. Normally, pacemakers are designed to regulate cardiac output by controlling the timing of events in the cardiac cycle and are usually set according to ECG criteria. ECG devices however measure only the heart rate and make no measure of cardiac output, a function of rate and volume, which is a measure of how much the heart pumps. The CW method provides a measure of the heart rate and total volume the heart pumps thereby providing more information required for optimisation of the settings of pacemaker devices. Obviously, testing in accordance with a wide variety of physiologic (exercise) conditions or pharmacologic testing is desirable.

Modern pacing devices are conceived to optimise cardiac performance. Cardiac performance is a function of rate and output volume. Current methods for setting parameters are generally based on rate setting from an ECG. The ultrasound device 12 provides both rate and volume information so that pacemaker timing of cardiac events can be optimised. In particular, biventricular pacing devices allow asynchronous activation of ventricular chambers. Indeed, the delay period between the activation of right and left ventricular chambers effect the optimal haemodynamic performance and varies with individual physiology and pathophysiology.

The use of the transcutaneous sensing of blood flow within the heart allows for the determination of optimal pacing delays in pacemaker devices leading to more appropriate use and effect of these devices.

Further, By carrying out a large number of tests on a large number of patients under a large number of different conditions, various indicies can be built up in guiding the system in setting the pacing rates for particular patient activities. The test can be carried out on a plurality of patients and the total set of results statistically combined, e.g. averaged for patient variables such as age, sex, weight etc.

Figure 6:
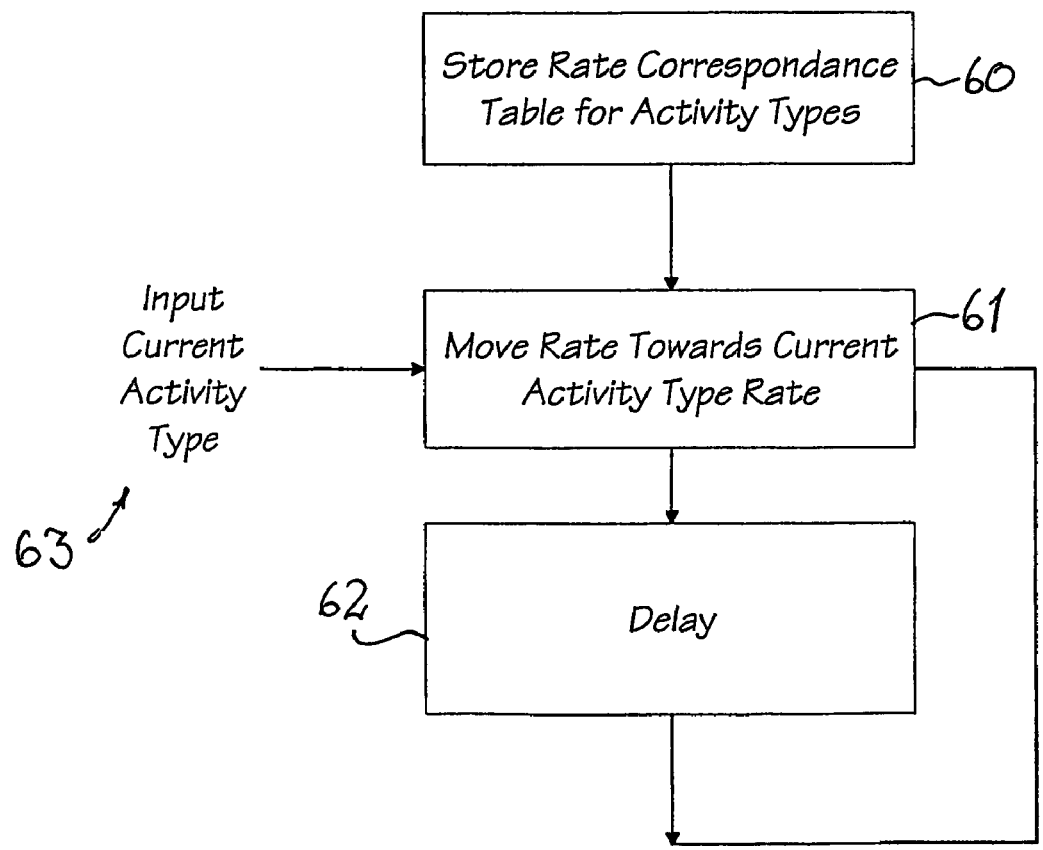

Upon conducting an analysis of flow rate with activity type, a determination can be made of the desirable flow rate for standard activity types measurable with the type of pacemaker device utilised. The desirable flow rate for each activity type can then be uploaded to the pacemaker device and utilised to tune the pacemaker's operation. For example, FIG. 6 illustrates a flow chart of one possible control loop within the pacemaker device. Utilising a precalculated stored table of correspondence between rate type and activity type 63, a given current activity type is input 63. The difference between a current rate and the activity type rate is calculated 61 and the current rate is slowly changed so that it is closer to the current activity rate. The system can operate in a feedback loop constantly with a predetermined delay 62.

Additionally, the invention as described herein can be used to improve understanding of the normal physiology and pathophysiology associated with cardiovascular function, exercise and pulmonary function.

It will be understood that the invention disclosed and defined herein extends to all alternative combinations of two or more of the individual features mentioned or evident from the text or drawings. All of these different combinations constitute various alternative aspects of the invention.

The foregoing describes embodiments of the present invention and modifications, obvious to those skilled in the art can be made thereto, without departing from the scope of the present invention.

The claims defining the invention are as follows:

1. A method of tuning a cardiac prosthetic pacing device, the method comprising the steps of:
   (a) monitoring the flow output from the heart utilizing a transcutaneous continuous wave Doppler signal directed at the heart to obtain a signal indicative of intra-cardiac blood flow velocity under a number of different operation conditions for a patient including walking and running;
   (b) constructing a table of correspondence between activity type and flow rate and storing said table on said cardiac prosthetic pacing device; and
   (c) using said table, adjusting the timing of pacing events by said cardiac prosthetic pacing device so as to optimise the flow from the heart under operational conditions.

2. A method as claimed in claim 1 wherein said monitoring is repeated under a number of different pharmalogical conditions for a patient.

3. A method as claimed in claim 1 wherein said monitoring is conducted on a number of patients.

4. A method as claimed in claim 3 wherein results from the number of patients are statistically combined.

5. A method as claimed in claim 4 wherein the statistical combination of results includes averaging for at least one of age, sex and weight.

6. A method as claimed in claim 1 wherein the adjustment of the timing of pacing events includes calculating a difference between a current rate and an activity rate obtained from said table and adjusting the timing of pacing events so that the current rate is closer to the activity rate.

7. A method as claimed in claim 6 wherein said adjustment operates in a feedback loop constantly with a predetermined delay.

* * * * *